United States Patent
Lin et al.

(10) Patent No.: US 9,398,895 B2
(45) Date of Patent: Jul. 26, 2016

(54) METHOD APPARATUS AND SYSTEM FOR ENHANCING NEEDLE VISUALIZATION IN MEDICAL ULTRASOUND IMAGING

(71) Applicant: General Electric Company, Schenectady, NY (US)

(72) Inventors: Yimeng Lin, WuXi (CN); Menachem Halmann, Bayside, WI (US); Feng Lin, WuXi (CN); Jianjun Guo, WuXi (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 14/846,271

(22) Filed: Sep. 4, 2015

(65) Prior Publication Data

US 2015/0374329 A1 Dec. 31, 2015

Related U.S. Application Data

(62) Division of application No. 13/592,034, filed on Aug. 22, 2012, now Pat. No. 9,149,253.

(30) Foreign Application Priority Data

Aug. 25, 2011 (CN) .......................... 2011 1 0270881

(51) Int. Cl.
*A61B 5/05* (2006.01)
*A61B 8/08* (2006.01)
(Continued)

(52) U.S. Cl.
CPC ................. *A61B 8/0841* (2013.01); *A61B 8/13* (2013.01); *A61B 8/5215* (2013.01); *A61B 8/54* (2013.01); *A61B 2019/5263* (2013.01); *A61B 2034/2063* (2016.02); *G03B 42/06* (2013.01)

(58) Field of Classification Search
CPC .... A61B 8/06; G01S 15/8915; G01S 15/8984
See application file for complete search history.

(56) References Cited

U.S. PATENT DOCUMENTS

| 4,869,259 A | 9/1989 | Elkins |
| 4,977,897 A | 12/1990 | Hurwitz |

(Continued)

FOREIGN PATENT DOCUMENTS

| CA | 2373295 A1 | 11/2000 |
| CN | 101467896 A | 7/2009 |

(Continued)

OTHER PUBLICATIONS

Bunting, "New ultrasound technology sharpens needle visibility: Imaging advance aids insertions into deep targets at steep angles", DOTmedbusiness news, Nov. 2010.

(Continued)

*Primary Examiner* — Mark Remaly
(74) *Attorney, Agent, or Firm* — GE Global Patent Operation; Marc A. Vivenzio

(57) ABSTRACT

The present invention discloses a method, apparatus and system for enhancing needle visualization in ultrasound imaging, said method comprising: a setting step for setting a scanning depth corresponding to a depth of a part or tissue target in a patient's body; and a determining step for automatically determining a needle frame steering angle and an ultrasound working frequency for needle frame collection based on the scanning depth. In the embodiments of the present invention, the needle frame steering angle and ultrasound working frequency for needle frame collection and the filter kernel for enhancing edge filtering of the collected needle frame are both dependent upon the scanning depth, and thereby can achieve enhancing needle visualization in ultrasound imaging for scanning at different depths without participation of the user or extra change of hardware.

9 Claims, 6 Drawing Sheets

(51) Int. Cl.
  *A61B 8/13* (2006.01)
  *A61B 8/00* (2006.01)
  *A61B 19/00* (2006.01)
  *G03B 42/06* (2006.01)

(56) References Cited

U.S. PATENT DOCUMENTS

| | | |
|---|---|---|
| 6,524,247 B2 | 2/2003 | Zhao et al. |
| 2013/0072785 A9 | 3/2013 | Guo et al. |
| 2013/0261432 A1 | 10/2013 | Guo et al. |

FOREIGN PATENT DOCUMENTS

| | | |
|---|---|---|
| CN | 102525547 A | 7/2012 |
| EP | 0952462 A2 | 10/1999 |
| EP | 1132049 A1 | 9/2001 |
| JP | 2008148914 A | 7/2008 |

OTHER PUBLICATIONS

Non-Final Rejection towards related U.S. Appl. No. 13/592,034 dated Nov. 7, 2013.
Final Rejection towards related U.S. Appl. No. 13/592,034 dated May 15, 2014.
"VirtuTrax Instrument Navigator", downloaded from http://www.civco.com/mmi/ultrasound/needle-tracking/tracking-needles/virtutrax-instrument-navigator-PID5105.htm on May 30, 2014.
"eTRAX Needle Tip Tracking System—14 GA", downloaded from http://www.civco.com/mmi/ultrasound/needle-tracking/etrax/eTRAX-Needle-Tip-Tracking-System---14GA.htm on May 30, 2014.
Non-Final Rejection towards related U.S. Appl. No. 13/592,034 dated Feb. 12, 2015.
Unofficial translation of Chinese Office Action and Search report issued from corresponding CN Application No. 201110270881.5 dated Jun. 5, 2015.

| 1 | 0 | 0 | 0 | 0 | 0 | 0 |
| 0 | 1 | 1 | 1 | 0 | 0 | 0 |
| 0 | 0 | 0 | 1 | 1 | 1 | 0 |
| 0 | 0 | 0 | 0 | 0 | 1 | 1 |
| 0 | 0 | 0 | 0 | 0 | 0 | 1 |

FIG. 4

| 1 | 1 | 0 | 0 | 0 | 0 | 0 |
| 1 | 1 | 1 | 0 | 0 | 0 | 0 |
| 0 | 1 | 1 | 1 | 0 | 0 | 0 |
| 0 | 0 | 1 | 1 | 1 | 0 | 0 |
| 0 | 0 | 0 | 1 | 1 | 1 | 0 |
| 0 | 0 | 0 | 0 | 1 | 1 | 1 |
| 0 | 0 | 0 | 0 | 0 | 1 | 1 |

FIG. 5

METHOD APPARATUS AND SYSTEM FOR ENHANCING NEEDLE VISUALIZATION IN MEDICAL ULTRASOUND IMAGING

CROSS-REFERENCE TO RELATED APPLICATIONS

This application is a divisional of U.S. patent application Ser. No. 13/592,034, filed on Aug. 22, 2012, which claims foreign priority benefits to Chinese Application No. 201110270881.5, filed on Aug. 25, 2011, all of which are incorporated by reference herein in their entireties.

BACKGROUND OF THE INVENTION

Embodiments of the present invention relate to an ultrasound imaging technique, more particularly to a method, apparatus and system for enhancing needle visualization in medical ultrasound imaging at different scanning depths.

In medical device ultrasound guidance application, the needle visualization in ultrasound image is paramount for the clinician to successfully perform an invasive ultrasound image guided procedure.

Needle visualization techniques in medical ultrasound systems, such as B steer, SteerXBeam and Expanded SteerXBeam, usually use one special additional frame called "needle frame" with fixed big steering angle and collected by applying fixed ultrasound working frequency to visualize and enhance the needle. If the needle guidance direction is vertical to the steering angle for needle frame, needle visualization is enhanced. Otherwise, the needle will disappear or fade in the ultrasound image.

For example, the U.S. Pat. No. 6,524,247 entitled "Method and system for ultrasound imaging of a biopsy needle" filed by Danhua Zhao et al. on May 15, 2001 discloses a method for enhancing real time visualization of a puncture needle, said method using a fixed scan angle (or a needle frame steering angle) to collect a needle frame. The Chinese patent application No. 201010624654.3 entitled "Method and apparatus for enhancing needle visualization in ultrasound imaging" filed by Jianjun Guo et al. on Dec. 27, 2010 discloses a needle frame with a large steering angle (e.g., 45°) and teaches that a plurality of frames collected by scanning at multiple angles, e.g., 25° and 45°, are combined to yield a needle frame, thereby achieving optimum effect.

However, as patients differ greatly in figures, the same parts or tissues (e.g., heart) have different scanning depths in different patients, and different parts or tissues have different scanning depths in the same patient as well. In the above-mentioned prior art, a fixed needle frame steering angle is always used for ultrasound scanning at different scanning depths, regardless of depth differences of different scanned parts or tissues in patients. As a result, when the fixed needle frame steering angle is used to scan a large (e.g. obese) patient, the needle is inserted into the patient's body substantially vertical to skin, such that the needle keeps substantially parallel to ultrasonic beam, thereby causing the needle to disappear or fade in the ultrasound image. Hence, the needle frame collected with fixed needle frame steering angle and ultrasound working frequency in the prior art cannot satisfy ultrasound guidance requirements at different depths.

Thus, it is necessary to provide a method, apparatus and system to avoid the aforesaid problems and defects.

BRIEF DESCRIPTION OF THE INVENTION

Embodiments of the present invention provide a method, apparatus and system operable to enhance needle visualization for scanning at different depths by applying a depth-dependent needle frame steering angle, ultrasound working frequency and edge enhancement filtering to a needle frame.

According to an embodiment of the present invention, a method for enhancing needle visualization in ultrasound imaging is provided. The method comprises setting a scanning depth corresponding to a depth of part or tissue target in a patient's body; and automatically determining a needle frame steering angle and an ultrasound working frequency for needle frame collection based on the scanning depth.

According to another embodiment of the present invention, an apparatus for enhancing needle visualization in ultrasound imaging is provided. The apparatus comprises a setting module configured to set a scanning depth corresponding to a depth of part or tissue target in a patient's body; and a determining module configured to automatically determine a needle frame steering angle and an ultrasound working frequency for needle frame collection based on the scanning depth.

According to another embodiment of the present invention, an ultrasound imaging system comprising an apparatus for enhancing needle visualization in ultrasound imaging is provided. The apparatus comprises a setting module configured to set a scanning depth corresponding to a depth of part or tissue target in a patient's body; and a determining module configured to automatically determine a needle frame steering angle and an ultrasound working frequency for needle frame collection based on the scanning depth.

BRIEF DESCRIPTION OF THE DRAWINGS

Embodiments of the present invention are specifically described hereunder with reference to the figures and in combination with the embodiments. The same or similar elements in the figures are represented with the same reference numerals. In the figures:

FIG. 4 illustrates a kernel configuration of an edge enhancement filter when the needle frame steering angle is 30°;

FIG. 5 illustrates a kernel configuration of an edge enhancement filter when the needle frame steering angle is 45°;

DETAILED DESCRIPTION OF THE INVENTION

Figure 1:
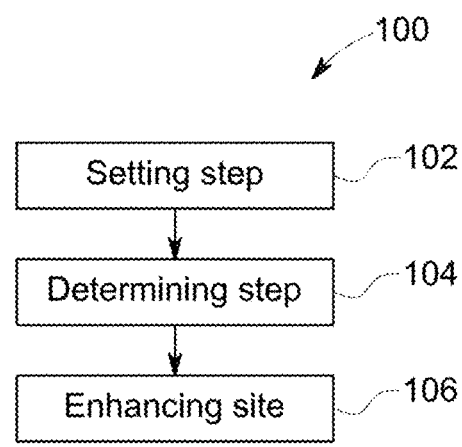
FIG. 1 illustrates a flowchart of a method for enhancing needle visualization in ultrasound imaging according to one embodiment of the present invention.

Many medical applications need ultrasound guidance of medical instruments like a needle to direct various invasive medical instruments to the part or tissue target within a patient's body. To direct the needle to the part or tissue target safely and rapidly, it needs to enhance visualization of the needle in the ultrasound image.

A Needle is a highly reflective object. When the scan angle is vertical or substantially vertical to the needle angle, the needle visualization in the ultrasound image is remarkable. In conventional medical imaging techniques, a needle frame is used to enhance visualization of the needle in the ultrasound image. A fixed big steering angle and a fixed ultrasound working frequency are usually used to collect a needle frame. In the case of implementing medical instrument ultrasound guidance on different patients, parameters including needle frame steering angle, ultrasound working frequency and filter settings will keep unchanged when the depth of the part or tissue target in the patient's body change, which influences enhanced visualization of the needle in the ultrasound image.

Hence, according to the technique raised in the present invention, parameters like needle frame steering angle, ultrasound working frequency and/or filter settings are configured to be dependent upon the scanning depth corresponding to the depth of the part or tissue target in the patient's body. In other words, according to the embodiments of the present invention, the needle frame steering angle and ultrasound working frequency for needle frame collection will change correspondingly when the scanning depth changes with the depth of the part or tissue target in the patient's body.

According to one embodiment of the present invention, the method for enhancing needle visualization in ultrasound imaging further comprises an enhancing step for performing edge enhancement filtering on a collected needle frame.

According to another embodiment of the present invention, a filter kernel for performing the enhancing step matches the determined needle frame steering angle for needle frame collection.

According to another embodiment of the present invention, a nonzero coefficient is defined along a needle direction in the filter kernel matching the needle frame steering angle for needle frame collection.

According to another embodiment of the present invention, a predefined needle frame steering angle and a predefined ultrasound working frequency corresponding to the scanning depth are searched in a pre-stored table when performing the determining step as the needle frame steering angle and ultrasound working frequency for needle frame collection.

According to another embodiment of the present invention, the pre-stored table comprises a plurality of predefined depth values, and a plurality of predefined needle frame steering angles and a plurality of predefined ultrasound working frequencies respectively corresponding to each of the plurality of predefined depth values.

According to another embodiment of the present invention, the predefined needle frame steering angle and predefined ultrasound working frequency corresponding to one of the plurality of predefined depth values that is equal or proximal to the scanning depth are determined as the needle frame steering angle and ultrasound working frequency for needle frame collection when performing the determining step.

According to another embodiment of the present invention, the shallower the scanning depth, the smaller the needle frame steering angle for needle frame collection and the higher the ultrasound working frequency for needle frame collection.

According to another embodiment of the present invention, the deeper the scanning depth, the larger the needle frame steering angle for needle frame collection and the lower the ultrasound working frequency for needle frame collection.

According to another embodiment of the present invention, the apparatus for enhancing needle visualization in ultrasound imaging further comprises an enhancing module for performing edge enhancement filtering on a collected needle frame.

According to another embodiment of the present invention, a filter kernel used by the enhancing module matches the determined needle frame steering angle for needle frame collection.

According to another embodiment of the present invention, a nonzero coefficient is defined along a needle direction in the filter kernel matching the needle frame steering angle for needle frame collection.

According to another embodiment of the present invention, the determining module is configured to search for a predefined needle frame steering angle and a predefined ultrasound working frequency corresponding to the scanning depth in a pre-stored table as the needle frame steering angle and ultrasound working frequency for needle frame collection.

According to another embodiment of the present invention, the pre-stored table comprises a plurality of predefined depth values, and a plurality of predefined needle frame steering angles and a plurality of predefined ultrasound working frequencies respectively corresponding to each of the plurality of predefined depth values.

According to another embodiment of the present invention, the determining module is further configured to determine the predefined needle frame steering angle and predefined ultrasound working frequency corresponding to one of the plurality of predefined depth values that is equal or proximal to the scanning depth as the needle frame steering angle and ultrasound working frequency for needle frame collection.

According to another embodiment of the present invention, the shallower the scanning depth, the smaller the needle frame steering angle for needle frame collection and the higher the ultrasound working frequency for needle frame collection.

According to another embodiment of the present invention, the deeper the scanning depth, the larger the needle frame steering angle for needle frame collection and the lower the ultrasound working frequency for needle frame collection.

According to another embodiment of the present invention, the apparatus for enhancing needle visualization in ultrasound imaging further comprises or communicates with a memory for storing the table.

According to an embodiment of the present invention, the present invention provides an ultrasound imaging system comprising an apparatus for enhancing needle visualization in ultrasound imaging according to another embodiment of the present invention.

In the method, apparatus and system according to the embodiments of the present invention, the needle frame steering angle and ultrasound working frequency for needle frame collection and the filter kernel for enhancing edge filtering of the collected needle frame are both dependent upon the scanning depth corresponding to the depth of the part or tissue target in a patient's body. When the scanning depth changes with the depth of the part or tissue target in the patient's body, the preferred needle frame steering angle and preferred ultrasound working frequency for needle frame collection will be adjusted automatically, and edge enhancement filtering dependent upon the scanning depth will be performed on the collected needle frame, thereby achieving enhanced needle visualization in ultrasound imaging for scanning at different depths without participation of the user, which facilitates improving the work flow of needle guidance in ultrasound imaging and saving the latency time.

FIG. 1 illustrates a flowchart of a method 100 for enhancing needle visualization in ultrasound imaging according to one embodiment of the present invention. As shown in the Figure, a scanning depth corresponding to the depth of the part or tissue target in a patient's body is set at step 102. For example, when a clinician estimates the depth of the part or tissue target in a patient's body at about 10 cm, he/she may set a scanning depth of about 15 cm via an interface such that the part or tissue target is approximately at a central position of the collected tissue frame and needle frame. Persons skilled in the art will appreciate that the above data are just for demonstrative purpose and in no way limit the present invention.

At step 104, the scanning depth corresponding to the depth of the part or tissue target in a patient's body set at step 102 automatically determines the needle frame steering angle and ultrasound working frequency for needle frame collection. For example, a predefined needle frame steering angle and a predefined ultrasound working frequency corresponding to the set scanning depth can be searched in the pre-stored table as the needle frame steering angle and ultrasound working frequency for needle frame collection. The pre-stored table may comprise a plurality of scanning depth values each corresponding to a predefined needle frame steering angle and a predefined ultrasound working frequency. Table 1 shows an exemplary tabulation.

| Scanning Depth (cm) | Needle Frame Steering Angle (°) | Ultrasound Working Frequency (MHz) |
|---|---|---|
| ... | ... | ... |
| 1.0 | 15.0 | 15.0 |
| 2.0 | 20.0 | 13.0 |
| 3.0 | ... | ... |
| 4.0 | 30.0 | 10.0 |
| 5.0 | ... | ... |
| 6.0 | 40.0 | 8.0 |
| ... | ... | ... |

Table 1 demonstratively provides a plurality of combinations of scanning depth values, predefined needle frame steering angles and predefined ultrasound working frequencies. Persons skilled in the art will appreciate that the various combinations of the three parameters as listed in the table are just for demonstration and in no way limit the present invention. For example, although the scanning depth values in the table increase by a step length of 1.0 cm, persons skilled in the art will appreciate that the depth values can in fact increase by any proper step length (e.g., 0.5 cm, 0.1 cm). The predefined needle frame steering angle and predefined ultrasound working frequency corresponding to a given depth value is dependent upon the attributes of relevant components (e.g., a probe) in the ultrasound imaging system. The needle frame steering angle and ultrasound working frequency corresponding to each of the depth values in Table 1 can be determined with experiments and/or simulation.

Usually the smaller the scanning depth value, the smaller the corresponding needle frame steering angle and the higher the corresponding ultrasound working frequency; on the contrary, the larger the scanning depth value, the larger the corresponding needle frame steering angle and the lower the corresponding ultrasound working frequency.

At step 104, if the depth value equal to the scanning depth corresponding to the depth of the part or tissue target in a patient's body set at step 102 is not found in the table, the predefined needle frame steering angle and predefined ultrasound working frequency corresponding to the depth value proximal to the scanning depth set in the table shall be determined as the needle frame steering angle and ultrasound working frequency for needle frame collection.

At the optional enhancing step 106, edge enhancement filtering is performed on the collected needle frame. The Chinese patent application No. 201010624654.3 entitled "Method and apparatus for enhancing needle visualization in ultrasound imaging" filed by Jianjun Guo et al. on Dec. 27, 2010 proposes a method for applying edge enhancement filtering technique to the collected needle frame with an edge enhancement filter. The contents of this patent application are integrally incorporated herein by reference. FIG. 4 illustrates a kernel configuration of an edge enhancement filter when the needle frame steering angle for needle frame collection is 30°. FIG. 5 illustrates a kernel configuration of an edge enhancement filter when the needle frame steering angle for needle frame collection is 45°. As shown in the figures, the edge enhancement filter kernel matches the needle frame steering angle for needle frame collection. That is, a nonzero coefficient is defined along the needle direction in the edge enhancement filter kernel, wherein the nonzero coefficient can be, for instance, 1 but is not limited to 1.

As stated above, when performing edge enhancement filtering on the collected needle frame, the edge enhancement filter kernel is configured according to the needle frame steering angle for needle frame collection determined at step 104, and the resulting edge enhancement filter kernel is then cross-correlated (convoluted) with the collected needle frame, thereby enhancing the needle signal in the needle frame and suppressing other tissue signals and artifacts in the needle frame. Besides, since the needle frame steering angle for needle frame collection is dependent upon the scanning depth corresponding to the depth of the part or tissue target in the patient's body, the edge enhancement filter kernel configured according to the needle frame steering angle is also concerned with the scanning depth, and thereby can provide a lower level of detection for shallower needles shown in FIG. 4 as well as a higher level of detection for deeper needles shown in FIG. 5.

Some embodiments of the present invention are further explained below in combination with FIGS. 2-3.

Figure 2:
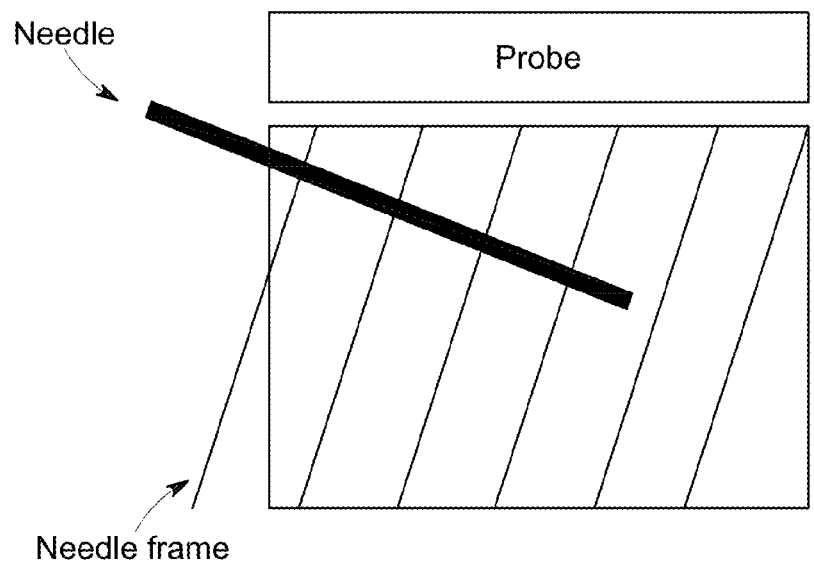
FIG. 2 is a schematic diagram illustrating a case of applying the method in FIG. 1 to a shallow depth according to one embodiment of the present invention.

FIG. 2 illustrates a case of application to a shallow depth (e.g., small or lean patients, or in vivo part or tissue target close to skin of a patient) according to one embodiment of the present invention. In this embodiment, the part or tissue target is about 1.0 cm deep in a patient's body. Accordingly, the scanning depth can be set to be about 2.0 cm. For shallow-depth applications, the part or tissue target and the needle are normally located in a shallower field of an ultrasound image. In this case, the needle frame steering angle for needle frame collection will be configured as a small one which can enhance the needle visualization in the ultrasound image and improve the overall ultrasound image quality. In this embodiment, the needle frame steering angle for needle frame collection is set to be 20.0°. In the meanwhile, a higher ultrasound working frequency will be used to increase ultrasound image resolution and needle appearance in such shallow-depth applications. In this embodiment, the ultrasound working frequency for needle frame collection is set to be the higher 13.0 MHz.

Figure 3:
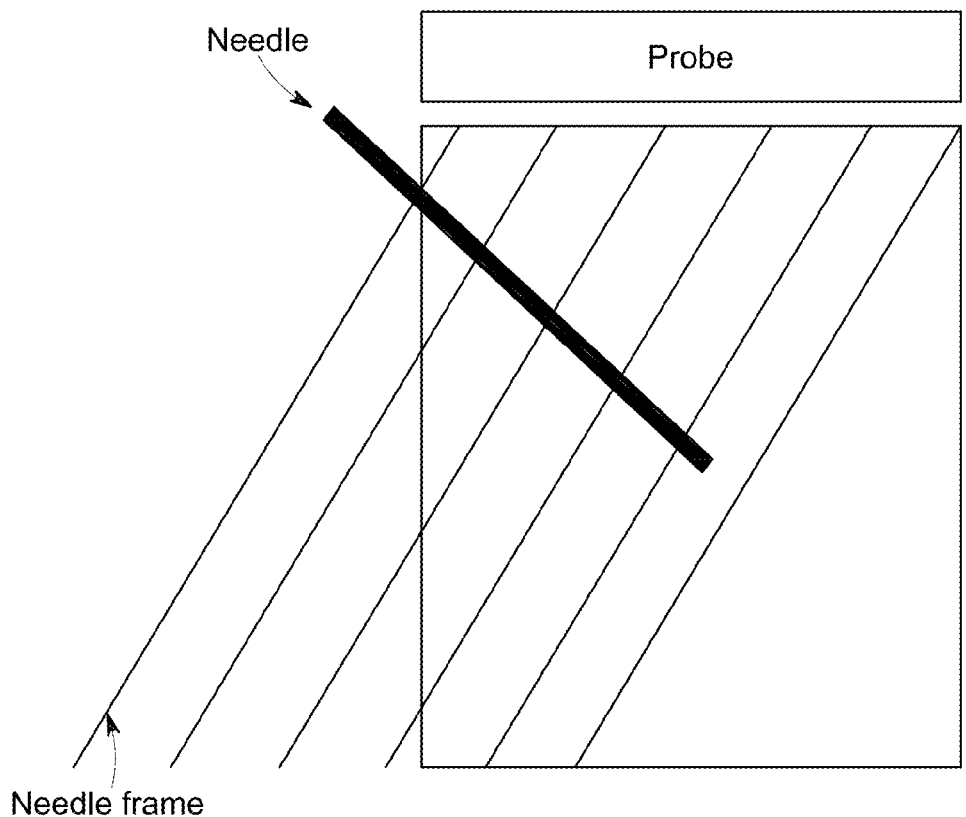
FIG. 3 is a schematic diagram illustrating a case of applying the method in FIG. 1 to a deep depth according to one embodiment of the present invention.

FIG. 3 illustrates a case of application to a deep depth (e.g., big or obese patients, or in vivo part or tissue target far from skin of a patient) according to one embodiment of the present invention. In this embodiment, the part or tissue targets are about 2.0 cm deep in a patient's body. Accordingly, the scanning depth can be set to be about 4.0 cm. For deep-depth applications, the part or tissue target and the needle in a far field of the ultrasound image will interest the clinician. In this case, the needle guidance is very steep with a big angle. Hence, the needle frame steering angle for needle frame collection should be configured as a large one to enhance ultrasound signal reflection from the needle. In this embodiment, the needle frame steering angle for needle frame collection is set to be 30.0°.

Limited by the acceptance angle of probe elements in the ultrasound imaging system, a large needle frame steering angle will bring considerable noise and artifacts for the collected needle frame. Therefore, a lower ultrasound working frequency is applied in deep-depth applications to expand the main lobe of a directivity function of ultrasound field, thereby decreasing noise and artifacts in the needle frame. In this embodiment, the ultrasound working frequency for needle frame collection is set to be the lower 10.0 MHz. Besides, a lower ultrasound working frequency in the deep-depth case will also increase the ultrasound penetration of in vivo tissues to the part or tissue target and the needle at a deeper position in a patient's body, and thus further enhance needle visualization in the ultrasound image.

Figure 6:
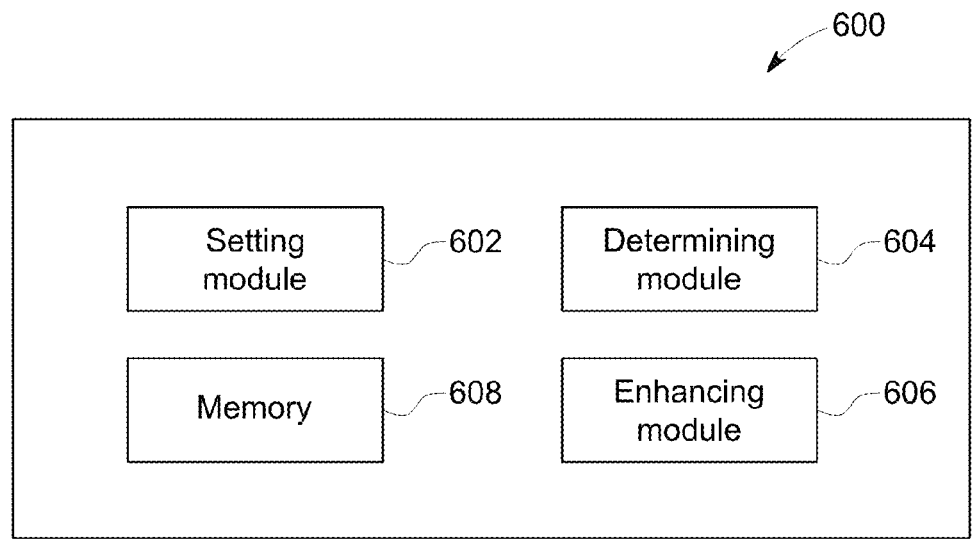
FIG. 6 is a schematic diagram illustrating an apparatus for enhancing needle visualization in ultrasound imaging according to one embodiment of the present invention.

FIG. 6 illustrates a modularization block diagram of an apparatus 600 for enhancing needle visualization in ultrasound imaging according to one embodiment of the present invention.

The apparatus 600 comprises a setting module 602 for setting a scanning depth corresponding to a depth of the part or tissue target in a patient's body; and a determining module 604 for automatically determining the needle frame steering angle and ultrasound working frequency for needle frame collection based on the set scanning depth. The shallower the set scanning depth, the smaller the needle frame steering angle for needle frame collection and the higher the ultrasound working frequency for needle frame collection. The deeper the set scanning depth, the larger the needle frame steering angle for needle frame collection and the lower the ultrasound working frequency for needle frame collection.

The determining module 604 is configured to search for a predefined needle frame steering angle and a predefined ultrasound working frequency corresponding to the set scanning depth in a table stored by a memory 608 as the needle frame steering angle and ultrasound working frequency for needle frame collection. Specifically, the determining module 604 is configured to use the predefined needle frame steering angle and the predefined ultrasound working frequency corresponding to the depth value equal or proximal to the set scanning depth in the table as the needle frame steering angle and the ultrasound working frequency for needle frame collection.

The apparatus 600 optionally comprises an enhancing module 606 for performing edge enhancement filtering on the collected needle frame, wherein a nonzero coefficient, e.g., 1 but not limited to 1, is defined along the needle direction in a filter kernel matching the needle frame steering angle for needle frame collection.

The apparatus 600 may further comprise or communicate with a memory 608 for storing a table necessary for determining the needle frame steering angle and the ultrasound working frequency for needle frame collection based on the set scanning depth. The table comprises a plurality of predefined depth values, and a plurality of predefined needle frame steering angles and a plurality of predefined ultrasound working frequencies respectively corresponding to each of the plurality of predefined depth values.

One or more modules in the apparatus 600 as shown in FIG. 6 can be implemented by software, hardware, firmware or combination(s) thereof.

Figure 7:
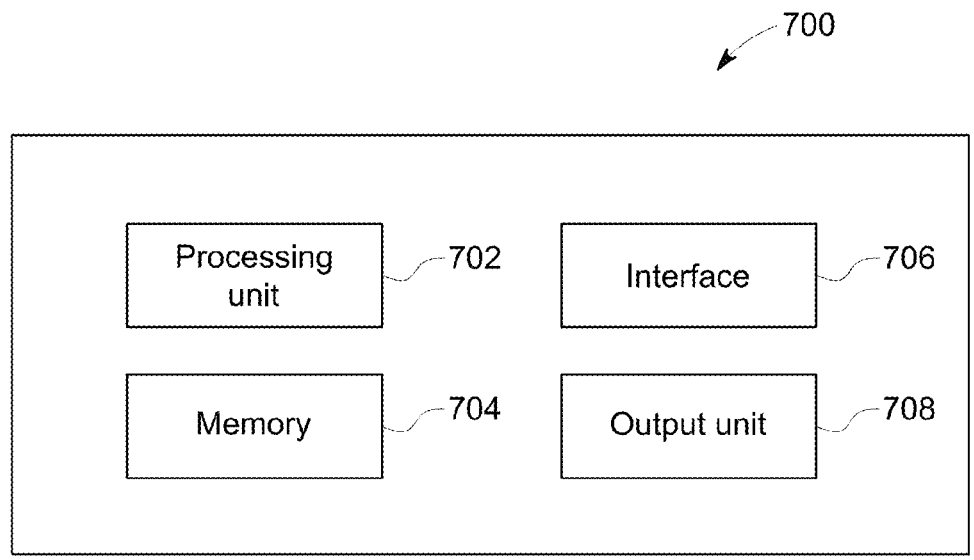
FIG. 7 is a schematic diagram illustrating another apparatus for enhancing needle visualization in ultrasound imaging according to one embodiment of the present invention.

FIG. 7 is a schematic diagram illustrating another apparatus 700 for enhancing needle visualization in ultrasound imaging according to one embodiment of the present invention. As shown in the figure, the apparatus 700 comprises a processing unit 702 such as MCU, DSP or CPU. The processing unit 702 may comprise one or more units to perform different steps of the method in FIG. 1. The apparatus 700 may further comprise or communicate with a memory 704 for storing the table mentioned above. The apparatus 700 optionally comprises an interface 706 for inputting a set scanning depth and collected needle image data; and an output unit 708 for outputting processed needle image data.

The apparatus 600 or 700 for enhancing needle visualization in ultrasound imaging according to the above embodiments can be implemented by software, hardware, firmware or combination(s) thereof in various ultrasound imaging systems.

Figure 8A:
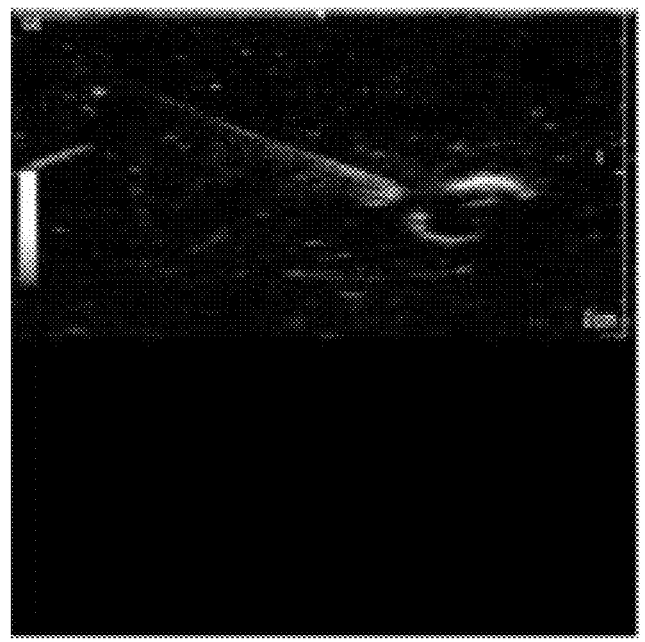
FIG. 8A illustrates a needle frame that is obtained according to the prior techniques in shallow depth applications.
Figure 8B:
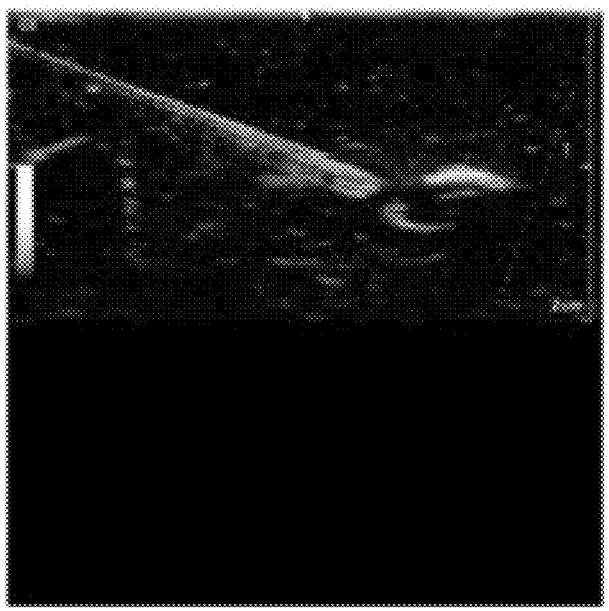
FIG. 8B illustrates a needle frame that is obtained according to the technique of the present invention in shallow depth applications.

FIG. 8A illustrates a needle enhancement image that is obtained according to the prior techniques in shallow depth applications; and FIG. 8B illustrates a needle enhancement image that is obtained according to the technique of the present invention in shallow depth applications. In the shallow depth applications, the scanning depth is set as 2 cm. As shown in the figures, the needle visualization obtained according to the technique of the present invention is remarkably enhanced as compared with the needle enhancement image that is obtained according to the prior techniques.

Figure 9A:
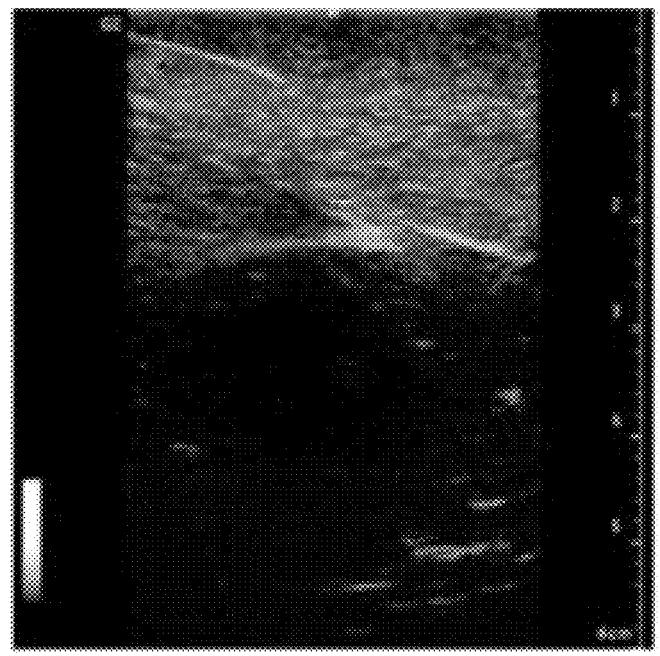
FIG. 9A illustrates a needle frame that is obtained according to the prior techniques in deep depth applications.
Figure 9B:
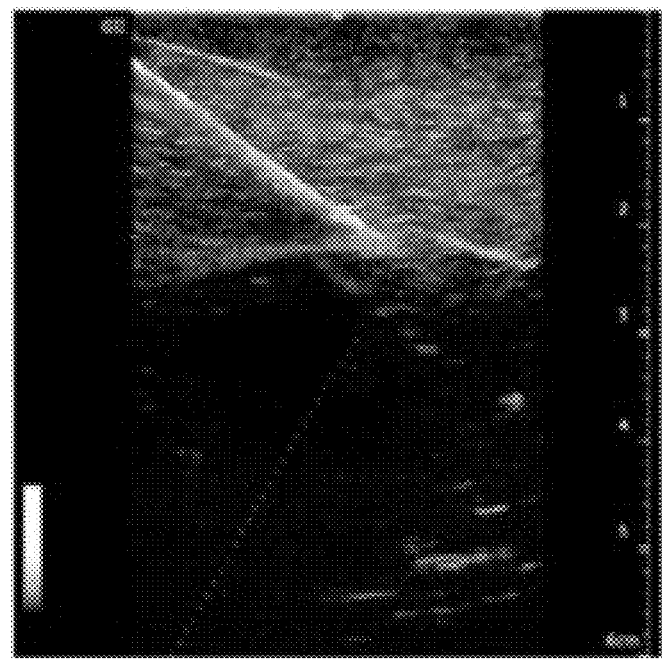
FIG. 9B illustrates a needle frame that is obtained according to the technique of the present invention in deep depth applications.

FIG. 9A illustrates a needle enhancement image that is obtained according to the prior techniques in deep depth applications; and FIG. 9B illustrates a needle enhancement image that is obtained according to the technique of the present invention in deep depth applications. In the deep depth applications, the scanning depth is set as 6 cm. As shown in the figures, the needle visualization obtained according to the technique of the present invention is remarkably enhanced as compared with the needle enhancement image that is obtained according to the prior techniques.

The foregoing is a detailed description of the present invention by way of specific embodiments. However, specific embodiments of the present invention should not be construed as limited to the description. It will be appreciated by those skilled in the art that various modifications, equivalent substitutions, and changes may be made to the present disclosure. For example, the function may be achieved by dividing one step or module in the above embodiments into two or more steps or modules; or on the contrary, the functions of two or more steps or modules in the above embodiments may be achieved within one step or module. As long as the alterations do not depart from the spirit of the present disclosure, they should be considered within the protection scope of the present invention. Besides, some terms in the description and claims of the present application are not limitative but descriptive. In addition, "one embodiment", "another embodiment" etc. used for many times above refer to different embodiments, and can definitely be entirely or partly incorporated in one embodiment.

The invention claimed is:

1. A method for enhancing needle visualization in ultrasound imaging, the method comprising: setting a scanning depth corresponding to a depth of a part or tissue target in a patient's body; and automatically determining a needle frame steering angle and an ultrasound working frequency for needle frame collection based on the scanning depth.

2. The method according to claim 1 further comprising performing edge enhancement filtering on a collected needle frame.

3. The method according to claim 2, wherein a filter kernel for performing edge enhancement filtering matches the determined needle frame steering angle for needle frame collection.

4. The method according to claim 3, wherein a nonzero coefficient is defined along a needle direction in the filter kernel matching the needle frame steering angle for needle frame collection.

5. The method according to claim 1, wherein automatically determining a needle frame steering angle and an ultrasound working frequency further comprises searching for a predefined needle frame steering angle and a predefined ultrasound working frequency corresponding to the scanning depth in a pre-stored table.

6. The method according to claim 5, wherein the pre-stored table comprises a plurality of predefined depth values, and wherein the pre-stored table comprises a plurality of predefined needle frame steering angles and a plurality of predefined ultrasound working frequencies respectively corresponding to each of the plurality of predefined depth values.

7. The method according to claim 6, wherein automatically determining a needle frame steering angle and an ultrasound working frequency further comprises determining the predefined needle frame steering angle and predefined ultrasound working frequency corresponding to one of the plurality of predefined depth values that is equal or proximal to the scanning depth.

8. The method according to claim 1, wherein the shallower the scanning depth, the smaller the needle frame steering angle for needle frame collection and the higher the ultrasound working frequency for needle frame collection.

9. The method according to claim 1, wherein the deeper the scanning depth, the larger the needle frame steering angle for needle frame collection and the lower the ultrasound working frequency for needle frame collection.

* * * * *